United States Patent [19]

Kawase et al.

[11] Patent Number: 5,143,847
[45] Date of Patent: Sep. 1, 1992

[54] ENZYME-FIXED BIOREACTOR

[75] Inventors: Mitsuo Kawase, Chita; Yasuko Yoshida, Nagoya; Hitoshi Yonekawa, Aichi, all of Japan

[73] Assignee: NGK Insulators, Ltd., Japan

[21] Appl. No.: 441,475

[22] Filed: Nov. 27, 1989

[51] Int. Cl.[5] .............................................. C12M 1/40
[52] U.S. Cl. .................................... 435/288; 435/299; 435/311; 55/475; 210/150; 210/263; 210/617; 422/211; 422/311
[58] Field of Search ............... 435/176, 288, 299, 311, 435/819, 313, 315, 316; 422/211, 219, 221, 236–239, 311; 55/475; 210/616, 617, 263, 150, 151; 261/DIG. 72

[56] References Cited

U.S. PATENT DOCUMENTS

| 3,374,052 | 3/1968 | Fan et al. ................. | 55/475 |
| 3,628,314 | 12/1971 | McCarthy et al. ................. | 422/218 |
| 3,838,977 | 10/1974 | Warren ................. | 422/179 |
| 4,016,044 | 4/1977 | Fresmel et al. ................. | 435/288 |
| 4,469,600 | 9/1984 | Frydman et al. ................. | 210/617 |

FOREIGN PATENT DOCUMENTS

| 299466 | 1/1989 | European Pat. Off. | |
| 0869938 | 1/1953 | Fed. Rep. of Germany | 55/475 |
| 1087700 | 5/1986 | Japan | 435/176 |
| 3190637 | 8/1988 | Japan | 435/176 |
| 0214929 | 8/1941 | Switzerland | 55/475 |
| 576996 | 11/1976 | Switzerland | |

OTHER PUBLICATIONS

Bailey et al., *Biochemical Engineering Fundamentals*, 2nd ed. New York, McGraw Hill, 1986, pp. 609–610.
Chemical Abstracts, vol. 105, 1986, p. 359, Abstract No. 111516d, Columbus, Ohio; & JP-A-61 115 493 (Shimadzu Corp.), Jun. 3, 1986.
Chemical Abstracts, vol. 111, 1989, p. 336, Abstract No. 92858x, Columbus, Ohio; & JP-A-63 190 637 (NGK Insulators, Ltd.) Aug. 8, 1988.
Chemical Abstracts, vol. 111, 1989, Abstract No. 35788a, Columbus, Ohio; & JP-A-63 91 083 (NGK Insulators, Ltd.), Apr. 21, 1988.
Chemical Abstracts, vol. 105, 1986, p. 402, Abstract No. 222219d, Columbus, Ohio; & JP-A-61 87 700 (Shimadzu Corp.), May 6, 1986.

*Primary Examiner*—Robert J. Warden
*Assistant Examiner*—William H. Beisner
*Attorney, Agent, or Firm*—Parkhurst, Wendell & Rossi

[57] ABSTRACT

An enzyme-fixed bioreactor, including a reaction column, enzyme-fixed catalyst particles uniformly and densely filled in the reaction column, the catalyst particles being composed of carrier sepiolite particles consisting essentially of sepiolite and an enzyme carried on the surface of the carrier sepiolite particles. The bioreactor has stable heat resistant and chemical properties, high productivity, and is economically superior to prior art, without fear of destruction of the catalyst, short path, and clogging in the reaction column.

3 Claims, 2 Drawing Sheets

FIG_2
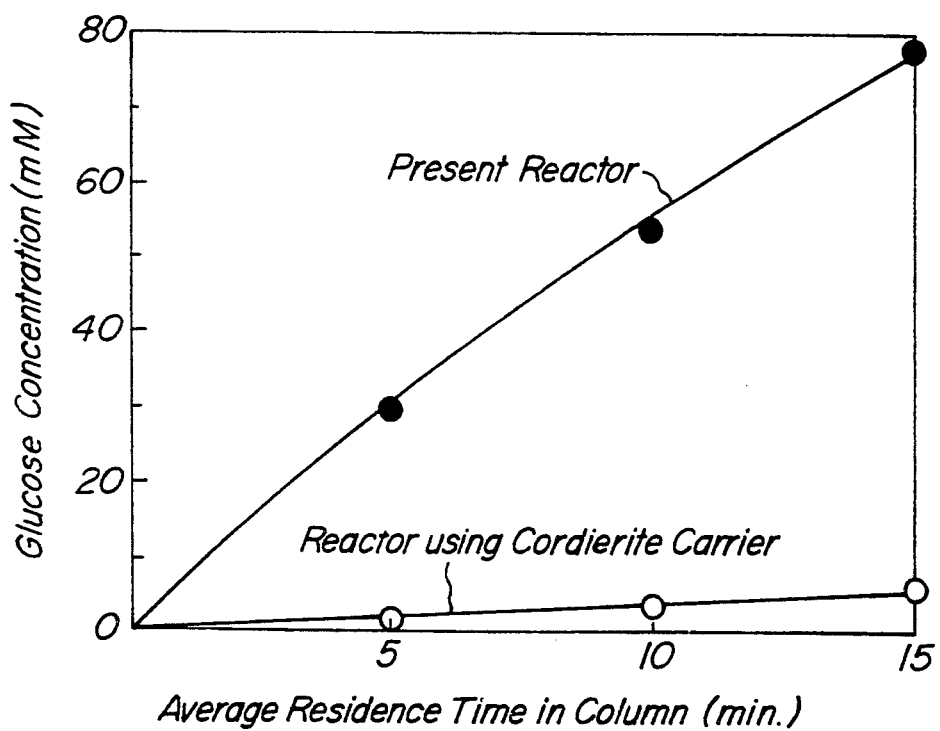

ENZYME-FIXED BIOREACTOR

BACKGROUND OF THE INVENTION

1. Field of the Invention

The present invention relates to an enzyme-fixed bioreactor using an enzyme as a biocatalyst for carrying out a biochemical reaction on an industrial level.

2. Related Art Statement

Recently, research of bioreactors containing in a reaction column an enzyme-fixed catalyst carrying an enzyme fixed on the carrier surface, has been progressed rapidly. For that purpose, various carriers have been proposed, such as high molecular organic substances, for example, carrageenan, or polyacrylamide, etc., or usual ceramic substances, for example, alumina, zirconia, etc. However, in reaction systems using a bioreactor having an enzyme-fixed catalyst, operations at high temperatures are often necessary to prevent contaminations of the bioreactor caused by undesirable micro organisms, and bioreactors using organic substances as carriers of the enzyme-fixed catalyst have drawbacks in that they are deficient in chemical stability and heat resistant property to endure the operations at high temperatures. Meanwhile, bioreactors using usual ceramic substances as carries of the enzyme-fixed catalyst have drawbacks in that the catalyst can carry thereon only a small amount of enzyme, so that the productivity of the bioreactor using such catalyst is insufficient, and the whole plant has to be increased in size or the reaction time has to be prolonged.

For solving these drawbacks, bioreactors using porous glass beads as a carrier of the enzyme-fixed catalyst have been of interest (Sumio Sakka "Application of Ceramics to Enzyme-fixed Carriers" in "Kagakusohchi" [3], 1983, pp.52-58). The porous glass beads have many advantages of small pores having a diameter of a few hundred Å by utilizing phase separation of glass resulting in a large specific surface area of 60–75 m$^2$/g, stable thermal and chemical properties, strong mechanical strength, and an outstanding capacity of enzyme that can be fixed on a unit amount of carrier as compared with conventional ceramic carriers. However, the porous glass beads have drawbacks in that they have to be produced by a complicated process of melting a glass at a high temperature of 1,500° C., reheating the melted glass to 500–600° C., and further heat treating the melted glass for a long time, so that they are very expensive as a carrier and difficult to use commercially in bioreactors of industrial scale. Thus, hitherto, a bioreactor having all of chemical and thermal stabilities, productivity, and economicity, has not been accomplished.

SUMMARY OF THE INVENTION

An object of the present invention is to obviate the above drawbacks.

Another object of the present invention is to provide an enzyme-fixed reactor containing in a reaction column a thermally and chemically stable enzyme-fixed catalyst composed of a carrier and an enzyme carried on the carrier in an outstandingly large amount per unit amount of the carrier as compared with that of the porous glass beads, and which can be produced cheaply.

The present invention is an enzyme-fixed bioreactor, comprising a reaction column, enzyme-fixed catalyst particles uniformly and densely packed or filled in the reaction column, the catalyst particles being composed of carrier sepiolite particles consisting essentially of sepiolite and an enzyme fixed on the surface of the carrier sepiolite particles.

The carrier sepiolite used in the present invention is obtained by pulverizing a raw sepiolite material consisting essentially of sepiolite or raw sepiolite stone to form sepiolite powder, optionally adjusting chemical composition and/or particle size distribution of the sepiolite powder, shaping the sepiolite powder to a desired form, such as particles, and firing the shaped powder at a temperature of about 300–1,100° C. A raw sepiolite stone is a lump of magnesium silicate fibers, which has a unique crystal structure of stacking talc fractions in a brick wall form, and has peaks at around 10 Å and 200 Å in pore size distribution. The inventors have ascertained that, if a raw sepiolite stone is fired, it loses crystalline water therefrom to assume a ceramic body, while changing its crystal structure and pore size distribution to have a large peak in a range of 200–400 Å of pores. Thus obtained carrier sepiolite has a specific surface area of 230 m$^2$/g which is more larger than that of the porous glass beads, so that it has a splendid functional ability of fixing enzyme thereon, as well as thermal and chemical stabilities due to ceramicsation thereof.

The carrier sepiolite is silanified on the surface by means of a silane-coupling agent, and then subjected to fix enzyme on the silanified surface to obtain an enzyme-fixed catalyst which is then packed in the reaction column of the bioreactor. Usual means can be adopted for fixing enzyme on the carrier sepiolite, and enzyme is fixed firmly on the surface of the carrier sepiolite consisting essentially of magnesium silicate at a high density by means of covalent bonds. Enzymes to be fixed on the carrier sepiolite are not limited at all, and illustrative examples thereof are, invertase, lactase, pepsin, trypsin, protease, glucoamilase, glucoseisomerase, aminoacylase, etc.

BRIEF DESCRIPTION OF THE DRAWINGS

For a better understanding of the present invention, reference is made to the accompanying drawings, in which:

FIG. 2 is a characteristic graph showing a relation between average residence time of a sucrose solution in the reaction column of the present bioreactor and glucose concentration at the outlet of the bioreactor.

Numberings in the drawings.

Figure 1:
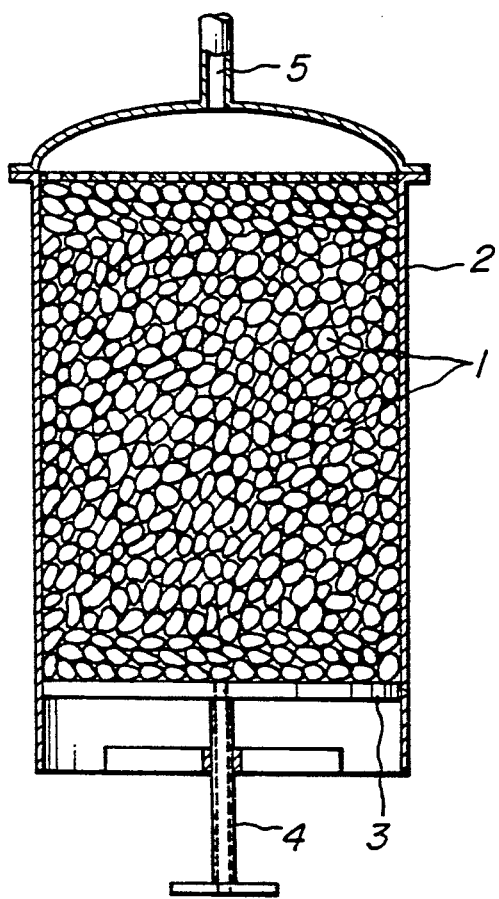
FIG. 1 is a schematic cross-sectional view of the enzyme-fixed bioreactor of the present invention.

1 .. enzyme-fixed catalyst
2 ... reaction column
3 ... movable plate
4 ... screw
5 ... discharge port

DESCRIPTION OF THE PREFERRED EMBODIMENTS

Referring to FIG. 1, an embodiment of the bioreactor of the present invention is shown, wherein the enzyme-fixed catalyst 1 is packed in the reaction column 2. The enzyme-fixed catalyst 1 using the carrier sepiolite has, a shortcoming in that it is fragile when rubbed against each other as compared with conventional catalysts using the porous glass beads or alumina ceramics. Therefore, the enzyme-fixed catalyst 1 according to the present invention should be uniformly and densely packed in the reaction column 2 so as to prevent relative movements thereof. For that purpose, the enzyme-fixed bioreactor of the present invention has preferably a movable plate 3 on the bottom and/or the top of the reaction column 2, and the plate 3 is movable by means of a screw 4, etc., to uniformly and densely pack the enzyme-fixed catalyst 1 in the reaction column 2, as shown in FIG. 1. In the embodiment shown in FIG. 1, a raw feed solution is supplied upwardly in the reaction column 2 through the interior of the screw 4, and an outlet solution containing reaction products is taken out from a discharge port 5 at the top of the reaction column 5. The uniformly and densely packed enzyme-fixed catalyst particles do not move in the reaction column 2, even in case of rinsing thereof for preventing decrease of the enzyme activity, resorbing of enzymes of decreased activity, and refixing of new enzymes on the catalyst carrier, etc., so that they are not broken or destroyed and do not cause troubles, such as, clogging or short path, in the reaction column 2.

Hereinafter, the present invention will be explained in more detail with reference to an example.

EXAMPLE 1

Carrier sepiolite particles of an average particle diameter of 0.3 mm are densely packed in a reaction column of an inner diameter of 20 cm and a height of 8 cm, and pressed in the reaction column by means of a movable plate arranged on the reaction column. Volume of the catalyst particles packed layer at this point is about 1 l. Another reaction column filled with carrier cordierite particles having the same average particle size as that of the sepiolite particles, is prepared, for comparison.

Then, the two reaction columns are fed with a 70% aqueous solution of ethanol at a flow rate of 30 ml/min, and the bioreactors are evacuate,,d. Subsequently, the reaction columns, are fed with distilled water of a flow rate of 100 ml/min to wash out ethanol therefrom, then with 50 mA of a buffer acetic acid aqueous solution (pH 4.0) of a flow rate of 100 ml/min to exchange the solution in the reaction columns. Thereafter, 2% commercial invertase/50 mA buffer acetic acid aqueous solution is circulated in the reaction columns at a flow rate of 30 ml/min for 3 hrs to fix invertase on the carrier surface. Excess invertase is recovered, and then 30% sucrose aqueous solution/50 mA buffer acetic acid aqueous solution (pH 4.0) as a substrate for the invertase is fed to the reaction columns in such flow rates that average residence times of the solution in the column becomes 5 min, 10 min, and 15 min, respectively, to measure glucose concentration of the solution at the outlet of the bioreactor, while keeping the reaction columns warm by passing warm water of 37° C. through jackets of the reaction columns.

The result are shown in FIG. 2. As seen from FIG. 2, the bioreactor of the present invention has a sucrose decomposition speed of about 30 times faster than the conventional bioreactor using the carrier cordierite particles. Thus, the bioreactor of the present invention has a productivity of 30 times larger than the conventional bioreactor of a same volume. If the productivity of the bioreactor of the present invention is held constant, i.e., to the same as that of the conventional bioreactor, the average residence time of the substrate in the reaction column or the volume of the bioreactor of the present invention can be made to 1/30 as those of the conventional bioreactor.

As apparent from the foregoing explanation, the bioreactor of the present invention using enzyme-fixed catalyst particles composed of carrier sepiolite particles and enzyme fixed on the surface of the carrier sepiolite particles uniformly and densely packed or filled in the reaction column has far superior productivity of the aimed product as compared with a conventional bioreactor using a ceramic catalyst carrier, as well as splendid heat resistant and chemical resistant properties. Also when comparing also the bioreactor of the present invention with the conventional bioreactor using porous glass beads, the bioreactor of the present invention, is economically superior, because the carrier sepiolite particles can be produced very cheaply or economically, so that even a large bioreactor can be produced with low expenditure. Moreover, if the enzyme-fixed catalyst particles are packed uniformly and densely in the reaction column by means of a movable plate, etc., breakage of the enzyme-fixed catalyst particles, short path and clogging, are prevented in the reaction column. Therefore, the enzyme-fixed bioreactor of the present invention obviates all the prior art problems, and is eminently useful industrially.

Although the present invention has been explained with reference to specific values and embodiments, it is of course apparent to those skilled in the art that various variations and modifications are possible without departing from the broad spirit and aspect of the present invention as defined in the appended claims.

What is claimed is:

1. A fluid-solid contact device, comprising:
   a contact column;
   solid particles contained in said column;
   a moveable piston member arranged at least at one end of said column for packing said particles uniformly and densely within said column, thereby preventing relative movement of said particles within said column when a fluid passes therethrough;
   a hollow piston rod member attached to said piston for introducing a fluid into said column to contact said particles; and
   means for discharging said fluid from said column after contacting said particles.

2. The device of claim 1, wherein said fluid is introduced into said column only through said hollow piston rod member.

3. The device of claim 1, wherein said particles consist essentially of fired carrier sepiolite particles having an enzyme carried on surfaces thereof.

* * * * *